(12) United States Patent
Kendall et al.

(10) Patent No.: US 10,203,463 B2
(45) Date of Patent: Feb. 12, 2019

(54) CORED WIRE, METHOD AND DEVICE FOR THE PRODUCTION OF THE SAME

(71) Applicant: Heraeus Electro-Nite International N.V., Houthalen (BE)

(72) Inventors: Martin Kendall, Zonhoven (BE); Robert Charles Whitaker, Chesterfield (GB); Marc Straetemans, Hechtel-Eksel (BE); Jack Childs, Workshop (GB); Dominique Feytongs, Hasselt (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 0 days.

(21) Appl. No.: 16/109,000

(22) Filed: Aug. 22, 2018

(65) Prior Publication Data
US 2018/0364432 A1 Dec. 20, 2018

Related U.S. Application Data

(63) Continuation of application No. 15/292,749, filed on Oct. 13, 2016.

(30) Foreign Application Priority Data

Oct. 14, 2015 (GB) .................................. 1518209.0

(51) Int. Cl.
*G01J 5/08* (2006.01)
*G01J 5/00* (2006.01)
(Continued)

(52) U.S. Cl.
CPC ............ *G02B 6/4415* (2013.01); *G01J 5/004* (2013.01); *G01J 5/021* (2013.01); *G01J 5/043* (2013.01); *G01J 5/0821* (2013.01); *G01K 1/146* (2013.01); *G01K 13/00* (2013.01); *G01N 33/206* (2013.01); *G02B 6/4402* (2013.01); *G02B 6/449* (2013.01);
(Continued)

(58) Field of Classification Search
None
See application file for complete search history.

(56) References Cited

U.S. PATENT DOCUMENTS

| 4,184,743 A | 1/1980 | Baker et al. |
| 4,484,963 A | 11/1984 | Anctil et al. |

(Continued)

FOREIGN PATENT DOCUMENTS

| CN | 1031897 A | 3/1989 |
| CN | 101075008 A | 11/2007 |

(Continued)

OTHER PUBLICATIONS

Search Report dated Mar. 16, 2016 in GB Application 1518209.

(Continued)

*Primary Examiner* — Ryan Lepisto
*Assistant Examiner* — Erin Chiem
(74) *Attorney, Agent, or Firm* — Panitch Schwarze Belisario & Nadel LLP

(57) ABSTRACT

A consumable cored wire for measuring a temperature of a molten steel bath includes an optical fiber and a cover laterally surrounding the optical fiber in a plurality of layers. One layer is a metal pipe, also called metal jacket or metal tube. An intermediate layer, also called filler, is arranged beneath the metal tube. The intermediate layer is a rope.

13 Claims, 8 Drawing Sheets

(51) Int. Cl.
*G01J 5/04* (2006.01)
*G01K 13/00* (2006.01)
*G01N 33/20* (2006.01)
*G01K 1/14* (2006.01)
*G01J 5/02* (2006.01)
*G02B 6/44* (2006.01)

(52) U.S. Cl.
CPC ......... *G02B 6/4433* (2013.01); *G02B 6/4436* (2013.01); *G02B 6/4488* (2013.01)

(56) References Cited

U.S. PATENT DOCUMENTS

| | | | |
|---|---|---|---|
| 4,723,831 | A | 2/1988 | Johnson et al. |
| 4,759,487 | A | 7/1988 | Karlinski |
| 5,310,964 | A | 5/1994 | Roberts et al. |
| 5,380,977 | A | 1/1995 | Yoshie et al. |
| 5,730,527 | A | 3/1998 | Takayama et al. |
| 6,770,366 | B2 | 8/2004 | Riche et al. |
| 7,197,199 | B2 | 3/2007 | Cuypers et al. |
| 7,690,841 | B2 | 4/2010 | Barbosa et al. |
| 7,748,896 | B2 | 7/2010 | Dams et al. |
| 7,906,747 | B2 | 3/2011 | Poulalion |
| 2002/0136511 | A1 | 9/2002 | Cecchi et al. |
| 2003/0059182 | A1 | 3/2003 | Johnson et al. |
| 2007/0268477 | A1 | 11/2007 | Dams et al. |

FOREIGN PATENT DOCUMENTS

| | | |
|---|---|---|
| CN | 101404190 A | 4/2009 |
| CN | 203259265 U | 10/2013 |
| DE | 19916235 A1 | 9/2000 |
| EP | 0306204 A1 | 3/1989 |
| GB | 1438074 A | 6/1976 |
| JE | 3712619 A1 | 10/1988 |
| JE | 19623194 C1 | 7/1997 |
| JP | H0815040 A | 1/1996 |
| JP | H09304185 A | 11/1997 |
| JP | H10176954 A | 6/1998 |
| JP | H11160155 A | 6/1999 |
| TW | 569047 B | 1/2004 |
| TW | I225167 B | 12/2004 |

OTHER PUBLICATIONS

Miracle et al., "Composites", ASM Handbook, vol. 21, 13 pgs (2001).
"E, R, and D Glass Properties Textiles Technical Data Sheet", Saint Gobain Vetrotex, 2 pgs (Mar. 2002).
Lamp et al., "Technical Steel Research Steelmaking Process: Innovative Continuous Online Determination of Steel Melt Temperature by Direct Optical Measurement in the Melt", European Commission, 9 pgs., (2005).
E.B. Shand, Engineering Glass, Modern Materials, vol. 6, Academic Press, New York, 1968.
Armil CFS, Refrasil Silica Cloth, X P882767329. Retrieved from the Internet URL:https:jjarmilcfs.com/wp-content/upload s/2815/87/Refrasil-Cloth-A.pdf [retrieved on Feb. 16, 2017.
Partial Search Report dated Mar. 6, 2017 in EP Application No. 16185690.1.
Fibre Optic Cable Catalogue, FibreFab, Version 7.11, 2011, downloaded from web page: https://www.hik-consulting.pl/shop/files/kable_swiatlowodowe_katalog.pdf, Download date: Feb. 2017, 42 pages.
Bentley Harris ST Fiberglass Braided Sleeving, Buy Heat Shrink, 2017, downloaded from webpage: http://buyheatshrink.com/contactus/contactus.php, Download date: Feb. 16, 2017, 5 pages.
Search Report dated Sep. 30, 2017 in TW Application No. 105130506.
Office Action dated Oct. 13, 2017 in TW Application No. 105130506.
Office Action dated Mar. 14, 2017 in U.S. Appl. No. 15/292,749.
Office Action dated Sep. 22, 2017 in U.S. Appl. No. 15/292,749.
Advisory Action dated Jan. 29, 2018 in U.S. Appl. No. 15/292,749.
Office Action dated Apr. 16, 2018 in U.S Appl. No. 15/292,749.
Office Action dated Nov. 30, 2018 in U.S. Appl. No. 15/292,749, by Kendall.

|  | E | A |
|---|---|---|
| SiO₂ | 56.99 | 43-74 |
| B₂O₃ | 6.12 | 0-8.5 |
| Al₂O₃ | 8.78 | 6-10 |
| MgO | 6.5 | 0.5-9 |
| CaO | 19.64 | 15-28 |
| Na₂O | 0.61 | 0-2.5 |
| K₂O | 0.00 | 0-0.5 |
| Fe₂O₃ | 0.13 | 0-0.3 |
| TiO₂ | 0.44 | 0-1 |
| F | 0.70 | 0-2 |

CORED WIRE, METHOD AND DEVICE FOR THE PRODUCTION OF THE SAME

CROSS-REFERENCE TO RELATED APPLICATIONS

This application is a Continuation of U.S. patent application Ser. No. 15/292,749 filed Oct. 13, 2016, which claims priority under 35 U.S.C. § 119(b) to British Application No. 1518209.0, filed Oct. 14, 2015, the disclosures of which are incorporated herein by reference in their entireties.

BACKGROUND OF THE INVENTION

The present invention relates to a consumable cored wire comprising an optical fiber surrounded by a cover for measuring a temperature of a molten steel bath. The present invention also refers to a method and a device for producing the cored wire.

JP H0815040 (A) describes a method that feeds a consumable optical fiber into liquid metal for measuring the temperature of molten metal baths. A similar method and apparatus for optical fiber measurements of molten metals is also described in U.S. Pat. No. 5,730,527. Consumable optical fibers of this kind are known, for example, from JP H11160155 (A). These are single metal jacketed optical fibers where the optical core is covered by a metal covering, typically stainless steel, that serves the purpose to stiffen the optical fiber such that it can be immersed into molten metal. Whereas these immersible optical fibers can penetrate beneath the molten surface, they suffer from a rapid deterioration. Improvements to these early consumable optical fibers comprise additional protection structures and are known, for example, from JP H10176954 (A). Here, the optical fiber is surrounded by a protective metal tube surrounded by a layer of plastic material. The covered optical fiber immersed into the molten metal is fed from a coil or spool at a predetermined rate that would expose the tip of the optical fiber to the metal when deeply immersed. The depth of immersion at the time of exposure is important for temperature accuracy. Therefore, preventing early destruction or moving the optical fiber tip to the measuring point quickly are necessary for accurate temperatures.

JPH09304185 (A) discloses a feeding rate solution where the speed of fiber consumption must be greater than the rate of devitrification, thereby assuring that a fresh optical fiber surface is always available. It has been found that the availability of a fresh fiber surface is essential for an accurate temperature measurement and this availability depends upon how the fiber is immersed into the molten metal. Multiple feeding schemes are likely to arise due to the numerous variety of conditions to which the fiber will be exposed during its introduction into and through various metallurgical vessels at various times during metals processing. When variation in the rate of devitrification can be minimized by improvement in the consumable optical fiber construction, the applicability of the technique can apply to a wider range of metallurgical vessels without customization of the feeding regime.

Multi-layered wire structures with a steel outer covering are used in steelworks to introduce doping substances selectively into the molten steel bath. These are typically called cored wires and are described in DE 19916235A1, DE 3712619A1, DE 19623194C1 and U.S. Pat. No. 6,770,366. U.S. Pat. No. 7,906,747 discloses a cored wire comprising a material which pyrolizes upon contact with a liquid metal bath. This technology applies to the introduction of generally uniform powdered substances into a molten bath and lacks teaching of how to make, manufacture and introduce a cored wire with an optical fiber into molten metal.

U.S. Pat. No. 7,748,896 discloses an improved optical fiber device for measuring a parameter of a molten bath. The device comprises an optical fiber, a cover laterally surrounding the optical fiber, and a detector connected to the optical fiber, wherein the cover surrounds the optical fiber in a plurality of layers. One layer comprises a metal tube and an intermediate layer arranged beneath the metal tube. The intermediate layer comprises a powder or a fibrous or granular material, wherein the material of the intermediate layer surrounds the fiber in a plurality of pieces. The intermediate layer is formed of silicon dioxide powder or aluminium oxide powder and may contain a gas producing material. The disclosed feature of the intermediate layer surrounding the fiber in a plurality of separate parts means, in the sense of the invention, that the construction in multiple parts exists in the operating state; in other words, during or after immersion in the molten bath to be measured such that the pieces of the intermediate layer remain separate and are separable during use.

The layered structure aids in keeping the optical fiber at a very low temperature for a relatively long time. Devitrification from elevated temperatures that will destroy the optical fiber is delayed. From a particular temperature onwards during immersion into molten metal, expansion of the gases of the intermediate layer forcibly remove the un-attached cover layers. The fiber is heated erratically to the equilibrium temperature in the molten metal bath, so that the measurement can then take place very quickly before the optical fiber or its end immersed in the molten metal bath is devitrified.

U.S. Pat. No. 4,759,487 and U.S. Pat. No. 5,380,977 discloses a method of producing a type of optical cored wire where an outer stainless steel jacket intimately surrounds the optical fiber. This type of cored optical fiber, known as armored optical fiber, lacks an intermediate layer insulation layer, and thus the use of this optical cored wire is limited and the method of production is unsuitable for the present invention.

An objective of the invention is to further improve a cored wire for measuring the temperature of a molten bath, and in particular molten steel.

BRIEF SUMMARY OF THE INVENTION

In one embodiment, the present invention relates to an optical cored wire comprising an optical fiber and a cover laterally surrounding the optical fiber. The cover surrounds the optical fiber in a plurality of layers. One layer is a metal pipe, also called metal jacket or metal tube, and maybe formed from a metal with a Fe content greater than 50%, preferably low carbon steel. An intermediate layer is arranged beneath the metal tube, and is also called filler. The intermediate layer is formed from a thermal insulating material which is gas porous having a melting point preferably in the temperature range of 1000° C. to 1500° C., more preferably at 1200° C. to 1400° C., such that the pieces of the intermediate layer are readily fluidized upon exposure to the molten metal temperatures. The intermediate layer is a rope or a structure composed of parallel fibers.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
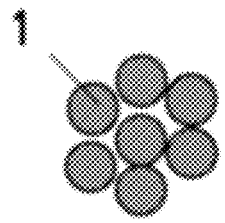
FIG. 1 is a cross-sectional view of a volumized strand consisting of a plurality of E-glass fibers.

The present invention relates to an optical cored wire comprising an optical fiber and a cover laterally surrounding the optical fiber. The cover surrounds the optical fiber in a plurality of layers. One layer is a metal pipe, also called metal jacket or metal tube. An intermediate layer is arranged beneath the metal tube and is formed from a thermal insulating material which is gas porous having a melting point preferably in the temperature range of 1000° C. to 1500° C., more preferably at 1200° C. to 1400° C., such that the pieces of the intermediate layer are readily fluidized upon exposure to the molten metal temperatures. The intermediate layer is a rope or a structure composed of parallel fibers.

A rope is a group of fibers, which are twisted or braided together in order to combine them into a larger and stronger form. In the classical sense of the word, a rope is composed of fibers that are collected into a yarn and multiple yarns are collected into a strand of which several strands are collected into a rope. The rope of the present invention maybe formed of a grouping of yarns and/or a grouping of strands with a singular chemical composition, or maybe comprised of a group of yarns or strands where several units of this grouping may be of different chemical compositions. Thus, the blending of yarns or strands of different chemical compositions can provide a simple manufacturing method of controlling the physical and chemical properties of an insulating layer where this layer has the form of a rope. A rope formed of multiple groupings of fibers ensures that the fibers cannot discharge from an opened end of the cored wire in advance at the time that the cored wire is fed into the melt. A discharge prior to the arrival at the melt would reduce the thermal isolation for the optical fiber, which would reduce the reliability of measurement results. No adhesive or resin is necessary for sticking the filler material together. Further, a rope with the optical fiber at its core guarantees a predictable central location means for the optical fiber and, hence, predicable thermal isolation properties in all lateral directions. As a result, the reliability of a temperature measurement is improved.

A continuous production is possible and allows the production of a cored wire having a length of at least 500 meters. A length of one, two and three and more kilometers is also possible without increasing the production effort. The length of one and more kilometers allows the measuring of temperatures of a molten steel bath with a minimized number of interruptions and worker involvement which increase the productive capacity and increases worker safety.

As an example, the temperature of a steel bath nearing completion of the refining process, where temperature measurements are most desirable, is about 1600° C. When the cored wire arrives at the molten steel bath, the outer metal tube will melt and the intermediate layer will fluidize and flow away immediately afterwards since the melting point of the intermediate layer material is much lower than the temperature of the molten steel bath.

It has been found that a molten gobular layer of material around the optical fiber flows away from the optical fiber at a predictable rate which is a function of its molten viscosity and the difference in density between it and the molten steel. In a practical sense, regarding the difference in density of the molten metal and molten filler (molten intermediate layer), although both are a function of temperature and composition, the magnitude of their difference in density is relatively constant within the application range of steelmaking. As the cored wire is immersed, the outer metal jacket melts away exposing the filler (intermediate layer) which subsequently melts and pools around the optical fiber. Since the melting temperature of the filler (intermediate layer) is substantially lower than the molten metal temperature once exposed, this guarantees that it will always be in a molten respectively fluid state, forms a molten gob and flows away.

It has become apparent that the restricted variation between the density of the steel and that of the molten gob results in a more predicable mechanism for exposing and renewing the fresh optical surface. The upward force of the displaced metal on the molten material of the intermediate layer (filler material) pushes the molten gob back and away from the optical fiber which stands extended from the gobular filler and forms a projection. As the feeding progresses, a sufficient quantity of molten filler accumulates at the base and a portion of this quantity is dragged with the extended optical core until the upward force of the molten metal upon the accumulated gob fractures the optical fiber at its unexposed base. The rate of exposed refreshed optical fiber is therefore more dependent upon the nearly constant density ratio gob/molten steel allowing a wide tolerance for the rate of feed. It has been found that retraction of the molten gob from the advancing optical fiber tip, specifically projection, leads to more repeatable detection opportunities.

In a preferred embodiment, the optical fiber is arranged in the center of the rope which further improves the quality and the reliability of the measurement results.

In a preferred embodiment, the yarns or strands of the rope (i.e., the structure composed of parallel fibers) are volumized. A rope within the meaning of the present invention is composed of a plurality of fibers with are collected into a yarn and multiple yarns comprise a strand and several strands are twisted together to form a rope. Volumized strands of yarns are treated in such a way, sometimes called texturizing, to have fibers irregularly oriented out of the fabric plane. The material is drawn through a nozzle in which an airstream creates turbulence in order to volumize the yarn or strand. A volumized rope decreases the apparent un-fused density while increasing the thermal isolation, and contributes to improved measurement results. The structure composed of parallel fibers is treated in a corresponding manner in order to volumize yarns or strands of the structure which comprises a plurality of parallel fibers.

In a preferred embodiment, the intermediate layer is formed from glass fibers, preferably from E-glass. This is an industrial common material and one suitable for the purpose of the present invention can be obtained from PPG Industries Cheswick, Pa., USA by the name of ET91415TEXO. This particular material is supplied in the form known to those in the art as a roving. In a first step, such a roving will be volumized. Two volumized rovings are then twisted into the yarn.

Glass fibers are useful thermal insulators because of their high ratio of surface area to weight. The density is low compared with the density of the molten steel bath, so that the softened glass fiber material in the molten steel bath will immediately flow upwards, which contributes to improved measurement results. The softening point of glass fibers is much lower than 1600° C. and thus much lower than the temperature of molten steel. The basis of E-glass is silica ($SiO_2$).

In a preferred embodiment, the intermediate layer is arranged between the metal tube and a tube formed from plastic, wherein the optical fiber is within the plastic tube. Improved measurement results are possible, especially when the outer diameter of the optical fiber is smaller than the inner diameter of the plastic tube. The preferred embodiment is a semi-tight buffer jacket. The general construction known in the art is either a 62.5/125 μm or alternately 50/125 μm graded index fiber placed in a 0.9 mm plastic tube in which the fiber is mechanically isolated from external forces. The material of the tube is generally plastic, and more specifically a polyamide, such as tradenames Nylon, or thermoplastic elastomers such as Hytrel, or similar materials as disclosed in a publication titled "Innovative continuous online determination of steel melt temperature by direct optical measurement in the melt." T. Lamp, et. al., Final Report EUR 21428, Contract no. 7210-PR/204, 2005, p 13-17. These plastics typically provide stiffening for the fiber against outside microbending influences. Suitable telecom optical fibers, as described, can be obtained from Huber and Suhner AG Degersheimerstrasse 14, CH-9100 Herisau DE. The plastic tube can be filled with moisture-resistant gel, which provides additional mechanical protection and a water barrier layer around the fiber. This filling material is generally petroleum or silicone-based compounds.

The density of the intermediate layer has a melted and unmelted density. Preferably, the fused density of the material of the intermediate layer is less than 5 $g/cm^3$, preferably less than 4 $g/cm^3$, more preferably between 2.0 and 3.5 $g/cm^3$. Since the density of molten steel is much higher, the material of the intermediate layer will flow immediately upwards upon melting of the outer metallic layer. Preferably, the ratio of the density of the liquid intermediate layer to that of the molten metal is between 0.25 and 0.45, and more preferably a ratio of 0.32 to 0.38. Since the intermediate layer is more or less a woven rope structure, it has a pre-melted density which is much less than its fused density and very insulative. The pre-melted density of the intermediate layer is 0.3 to 1.7 $g/cm^3$, more preferably between 0.4 and 1.0 $g/cm^3$. The pre-melted density is such that from the interface between the melted gob and the remaining unmelted intermediate layer is gas porous and permits the passage of combustion products of the intermediate layer in a direction opposite the fused intermediate layer material. Thus, improved measurement results are possible.

A method for producing the cored wire comprises the steps:
feeding an optical fiber through the axis of rotation of a twisting machine;
feeding strands of material fiber parallel to the axis of rotation to form a core with the optical fiber at its center;
twisting material fiber strands around the core by the twisting machine to form a rope alternating clockwise and counterclockwise with successive layers of strands;
forming from a strip of metal a band having a U-like or divided circle cross section by a pipe forming machine;
feeding the rope into the U-like or divided circle cross section of the metal band; and
forming the U-shaped metal band to encircle the pipe about the fiber rope by the pipe forming machine.

The method allows a continuous production of cored wires having a length of more than 500 meters, one, two or three kilometers without great production efforts.

A device for carrying out the method comprises a rope twisting machine with the capability of concurrently twisting alternate layers of fiber in both clockwise and counterclockwise directions, a pipe forming machine having a first section which forms a metal band having a U-like or divided circle cross section, and a feeding device which feeds the rope produced by the rope twisting machine into the U-like or divided circle cross section, wherein the pipe forming machine further forms a pipe from the U-like or divided circle cross section comprising the rope.

The device comprises a section which forms a mechanical closure for the pipe which is either an overlapped seam or alternately a lock seam. No further material is necessary for the production of the pipe, thus avoiding the presence of a further material which may influence a temperature measurement in a disturbing manner. This pipe, the outer metal jacket, protects the optical fiber at the beginning of a temperature measurement.

In a preferred embodiment, the device comprises a plurality of rolls which form the metal band in a stepwise manner. A very reliable production of the cored wire is possible.

Figure 2:
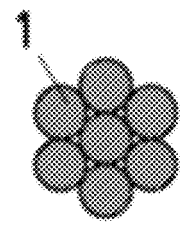
FIG. 2 is a cross-sectional view of a non-volumized strand consisting of a plurality of E-glass fibers.

FIGS. 1 and 2 show cross-sectional views of a strand which consists of a plurality of E-glass fibers 1. The strand shown in FIG. 1 is volumized. The strand shown in FIG. 2 is not volumized. For this reason, the pattern of the fibers of FIG. 1 is less regular than the pattern of the fibers 1 of FIG. 2. Further, the volumized fibers 1 shown in FIG. 1 are less compact compared with the fibers 1 shown in FIG. 2.

Figure 3:
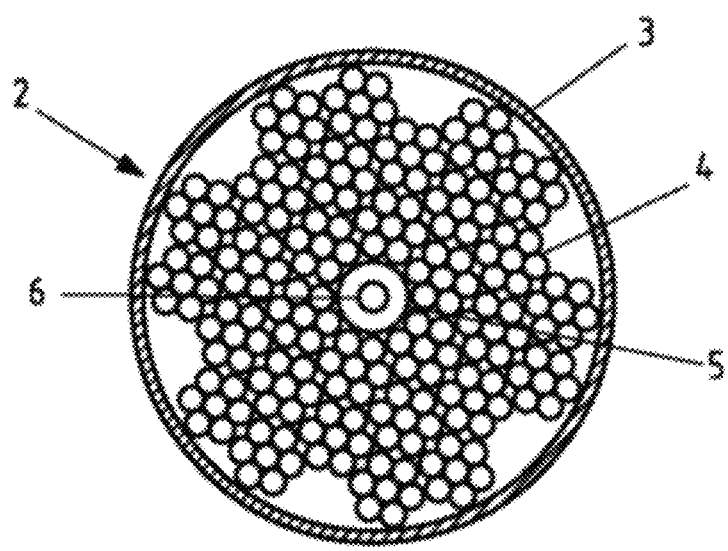
FIG. 3 is a cross-sectional view of a cored wire.

FIG. 3 shows a cross-sectional view of a cored wire 2 (seam not shown) comprising an outer metal coat (metal jacket) 3, a plurality of strands 4, an inner plastic tube 5 (also called semi tight jacket), and an optical fiber 6 within the plastic tube 5. The outer circumference of the optical fiber 6 is smaller than the inner diameter of the plastic tube 5. The strands 4 are volumized and formed from a plurality of E-glass fibers. The strands 4 are layered around the plastic tube 5 and form a rope. The plastic tube 5 is in the center of the rope 6 and within it. The number of strands illustrated in FIG. 3 are merely to show how multiple strands are applied to create the rope structure.

Figure 3A:
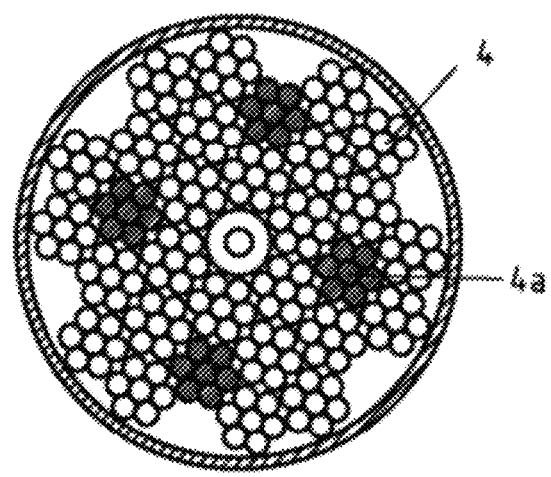
FIG. 3a is a cross-sectional view of a cored wire with a blended intermediate layer.

FIG. 3a shows a cross-sectional view of a cored wire 2 (seam not shown as depicted in FIG. 3) comprising an outer metal coat (metal jacket), a plurality of strands 4, and a plurality of strands of and alternate chemistry 4a, an inner plastic tube (also called semi tight jacket), and an optical fiber within the plastic tube. The number of strands illustrated in FIG. 3a are merely to show how multiple strands of different chemistries maybe applied to create the rope structure of an alternates physical and chemical properties.

Figure 4:
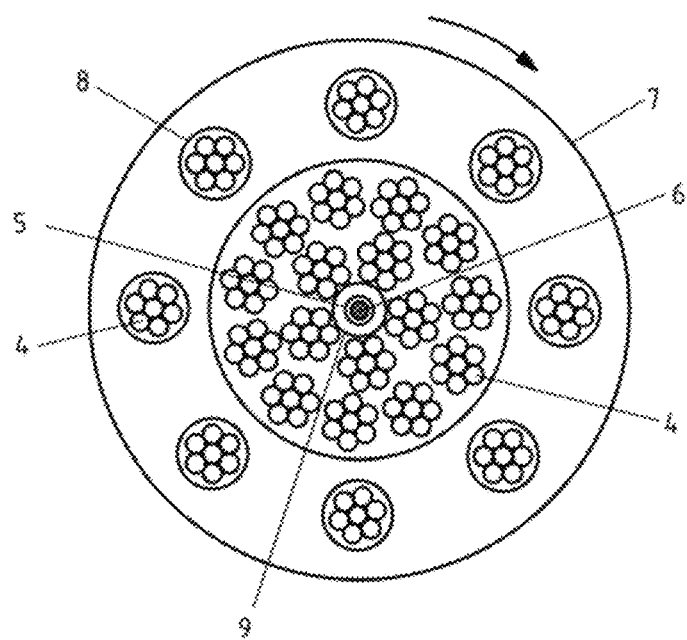
FIG. 4 is a front view of a single wheel twisting machine.

FIG. 4 is a front view of a wheel 7 of a single wrap twisting machine. The wheel is rotatably mounted by its hollow axis 9 and can rotate in the clockwise direction driven by a motor drive. The wheel 7 comprises a plurality of guide holes 8 arranged its circumference. The optical fiber and the plastic jacket 5 are fed through the hollow axis 9. Multiple strands 4 are fed parallel to the hollow axis collecting about the plastic jacket 5 to form a core. A strand 4 is fed through each guide hole 8. As wheel 7 is rotated, for example clockwise, the captured strands of each guide hole are rotated in the same direction. As the core moves through the die 10, depending upon the turning speed of the wheel, a twisted outer wrap of fibers encircles the core of bundled parallel fibers. The preferred speed results in the wrapping of 1 strand 1 turn per 100 mm of rope length.

Figure 4A:
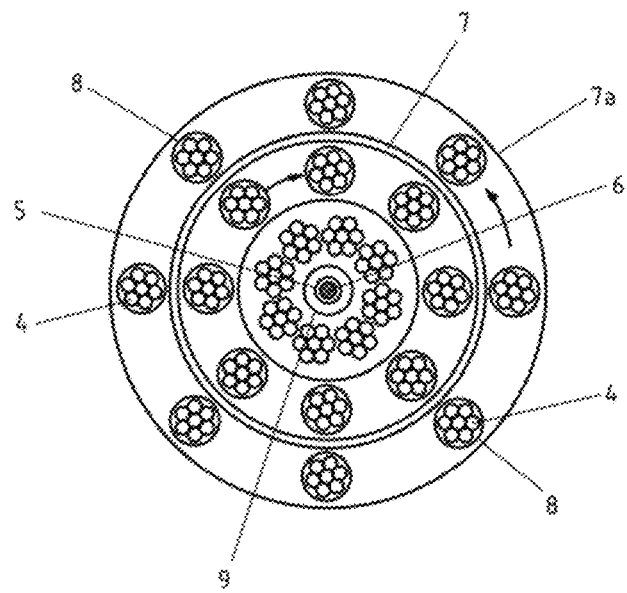
FIG. 4a is a front view of a dual wheel twisting machine.

FIG. 4a is a front view of a dual wheel twisting machine. The wheels 7 and 7a are rotatably mounted by its hollow axis 9 and can rotate concurrently in the clockwise and counterclockwise direction each driven by a motor drive. The reference to the clock are taken when facing the wheel and the rope being formed towards the observer. The wheels 7 and 7a comprise a plurality of guide holes 8 arranged their circumference. The optical fiber and the plastic jacket 5 are fed through the hollow axis 9. Multiple strands 4 are fed parallel to the hollow axis collecting about the plastic jacket 5 to form a core. A strand 4 is fed through each guide holes 8. As wheel 7 is rotated, for example clockwise, the captured strands of each guide hole are rotated in the same direction. As the core moves through the die 10, depending upon the turning speed of the wheel, a twisted outer wrap of fibers encircles the core of bundled parallel fibers. Wheel 7a, at the same time, is rotated counterclockwise. Strands captured by the guide holes 8 of wheel are now wrapped in the opposite direction as those of wheel 7. In both single and double wheel wrapping machines, one skilled in the art will recognize that the feed spools of material fiber comprising these ropes are mounted to and adjacent to the twisting wheel in order to supply the strands without wrapping prior to the collecting die.

Figure 5:
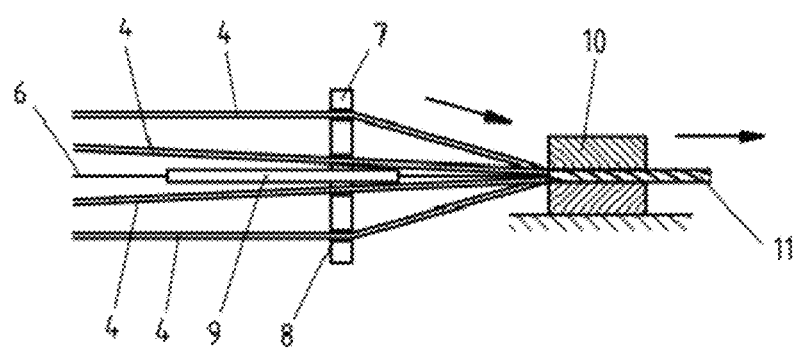
FIG. 5 is a side view of a twisting machine.

FIG. 5 is a side view of the twisting machine illustrating the forming of a rope 11 by rotation of the wheel 7. The rope 11 may be fed through a collecting die 10, for example. The arrows show the feeding direction of the strands 4, the optical fiber 6 together with the loose jacket 6 and the rope 11.

Figure 6:
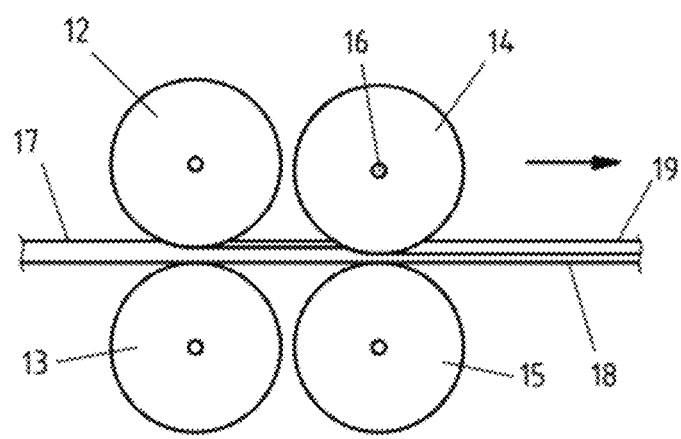
FIG. 6 is a side view of a first section of a pipe forming machine.

FIG. 6 is a side view of the beginning of a pipe forming machine comprising a plurality of rolls 12, 13, 14, 15 which are rotatably mounted by its axis 16.

Figure 7:
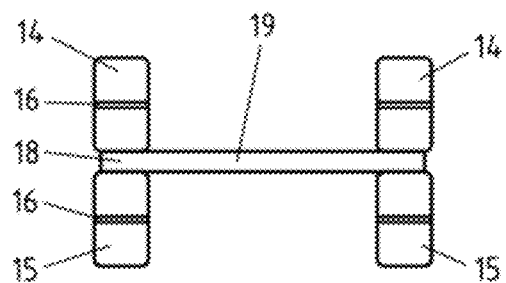
FIG. 7 is a front view a first section of a pipe forming machine.

FIG. 7 is a corresponding front view. One or more of the rolls 12, 13, 14, 15 may be driven by a motor drive. This is also true for the further rolls of the pipe forming machine. The rolls 12, 13, 14, 15 are arranged in pairs. The gap between a first pair 12, 13 is smaller than the gap between a second pair of rolls 14, 15. Pulling and despoiling a metal band from a coil, the two lateral border areas 18 of a metal band 17 are fed through the gaps. In this way, the pipe forming machine pulls the coil as well as pushes the border areas 18, preferably in a stepwise manner, forward through the metal forming machine.

Figure 8:
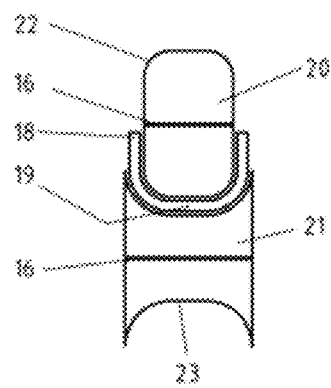
FIG. 8 is a front view of a second section of the pipe forming machine.

The following section of the pipe forming machine comprises one or more pairs of rolls forming the middle area of 17 in an arc-like manner as a rule step by step. FIG. 8 illustrates one pair of rolls 20 and 21 which are rotatable mounted by its axis 16. The circumference area 22 of the upper roll 20 is rounded. The circumference area 23 of the lower roll 21 is adapted to the rounded circumference area 22 so that there is a U-shaped or divided circle shaped gap between the pair of rolls 20, 21. The middle area of the metal band 17 is fed through this U-shaped or semicircle shaped gap, as shown in FIG. 8, forming a U shaped portion 19 of metal band 17. In order to form a U-like or a similar cross-section step by step, there is a plurality of pairs of rolls. The first pair forms for example a divided circle with a large diameter. The next pair of rolls reduces the diameter and so on. At the end of this section of the pipe forming machine, the cross section of the metal band 19 with border edges 18 looks like an "U", a semi-circle, a divided circle and the like.

Figure 9:
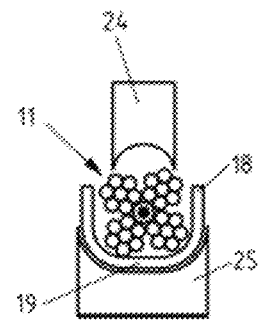
FIG. 9 is a front view of a feeding section for a rope.

Next, as shown in FIG. 9, there is a feeding section feeding the rope 11 into the formed metal band 18, 19. The feeding section comprises a pair of feeding elements 24, 25 which feeds the rope 11 to the bottom of the formed metal band 18, 19 as shown in FIG. 9. The feeding elements 24, 25 of the feeding section may have the form of rotatably mounted wheels. However, fixed mounted feeding elements 24, 25 are also possible.

Figure 10:
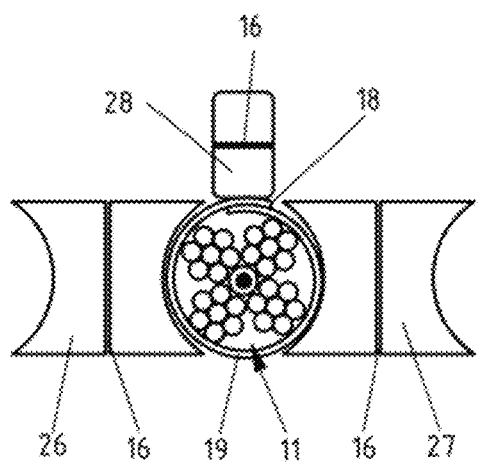
FIG. 10 is a front view of a next section of the pipe forming machine for forming a lap seam.

The next section of the pipe forming machine forms the middle section 19 into a circle as a rule step by step. This section comprises one or more pair of rolls. The circumference areas of such a pair of rolls equals more and more a circle in order to bring the middle area step by step into the form of a circle. An example for an appropriate roll 26, 27 is shown in FIG. 10 which forms the middle section 19 in a circle-like manner. One or more rolls, such as 28, may first press the flattened border areas 18 together as soon as the middle section is in the form of a circle. Ironing roll 28, for pressing the flattened border areas 18 together is also shown in FIG. 10. This is the preferred mechanical closure of the pipe with an overlap seam of 3-4 mm.

The flattened border areas 18 are not necessary. Thus, in an embodiment of the present invention, the thickness of the metal band remains uniform.

Figure 11:
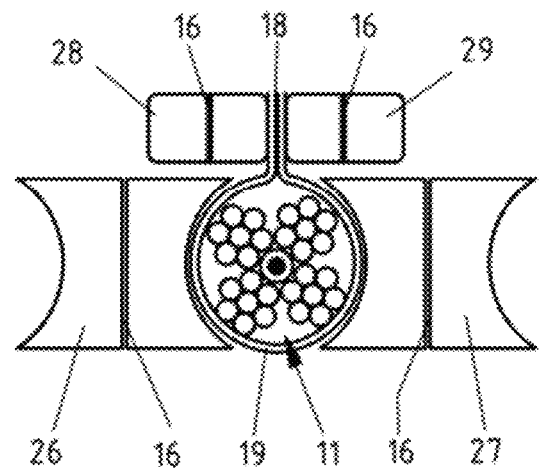
FIG. 11 is a front view of a next section of the pipe forming machine for forming an alternate mechanical closure for the pipe-a lock seam.
Figure 11A:
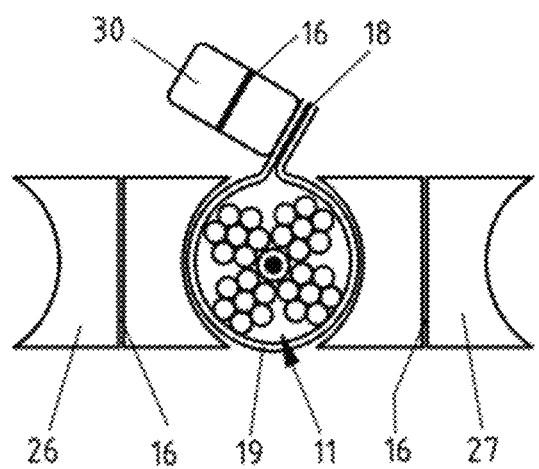
FIG. 11a is a front view of a next section of the pipe forming machine showing a fold over section of the alternate mechanical closure for the pipe.
Figure 11B:
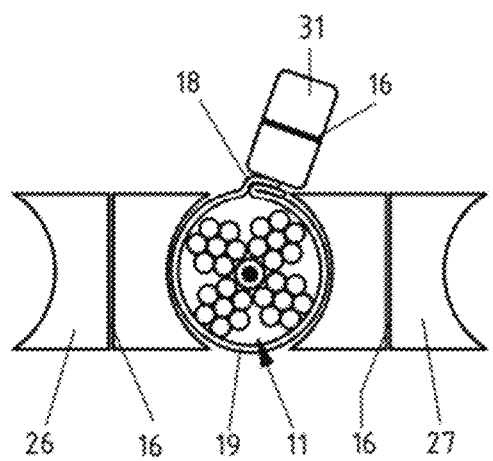
FIG. 11b is the end of the pipe forming machine for forming a levelling step for an alternate mechanical closure for the pipe.

FIGS. 11, 11a and 11b show the mechanical step of closing the tube in a lock seam, one of several know seam methods suitable for the practice of the present invention. FIG. 11 shows the border areas 18 pushed together by the rollers 28 and 29 forming a raised ridge. The next and last section of the pipe forming machine pushes the flattened border areas 18 against the outer circumference of the middle section 19, preferably step by step, for closing the pipe. This section comprises appropriate rolls 30, 31 which bend the flattened border areas 18 in a corresponding manner, step by step, as shown in FIGS. 11a and 11b.

Figure 12:
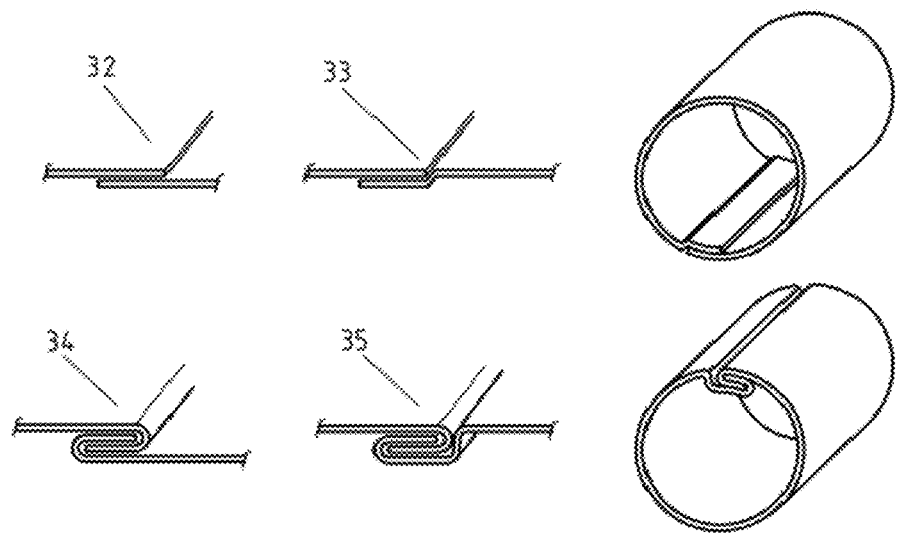
FIG. 12 is a view of common pipe seams and an example of the pipe formed.

One of the two border areas may have the form of a hook which holds the further border area in order close the pipe in a more reliable manner as shown in FIG. 12.

Figures 13, 14:
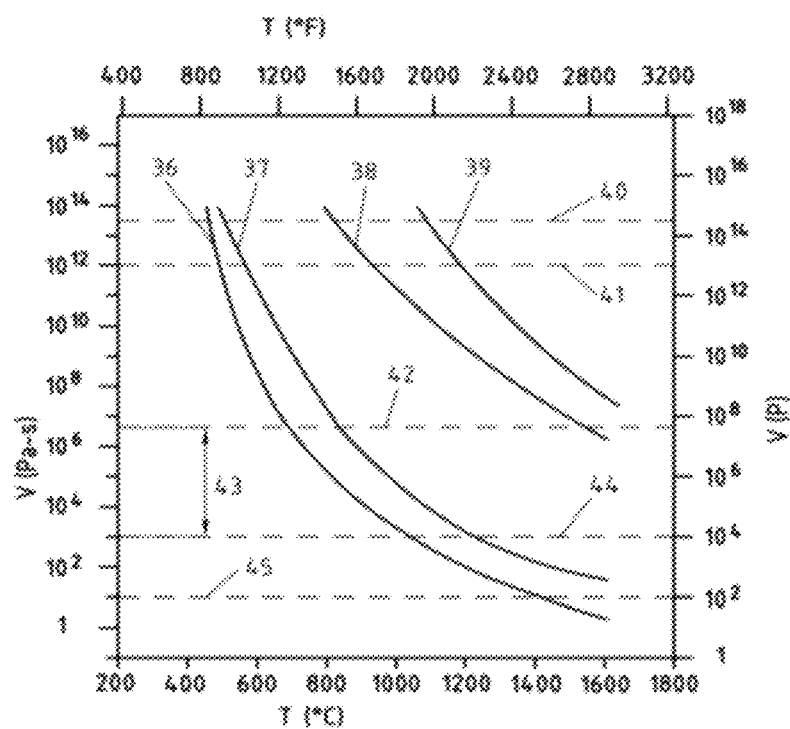
FIG. 13 is a table of the approximate E-glass composition in mol %.
FIG. 14 is a graphical depiction of the relationship of viscosity to temperature and general temperature range for the descriptive property of glasses.

FIG. 13 shows an appropriate composition for the fibers formed from E-glass. However, further compositions of glasses and/or mixtures of glasses and ceramic fibers are possible and can be formulated by substituting strands of fibers of the rope.

In FIG. 14, the relationship of logarithm viscosity and temperature is graphed. This information is taken from E. B. Shand, *Engineering Glass, Modern Materials*, Vol. 6, Academic Press, New York, 1968, p. 262.

In an example, the present invention refers to a plastic jacketed optical fiber surrounded with a volumized low alkali, low liquidus temperature glass, covered with an outer jacket of low carbon steel.

The material of the intermediate layer is known in the industry as E-glass, although other low melting materials are acceptable. One will appreciate that fused materials, such as the glasses of the intermediate layer, do not experience a distinct melting point as crystalline materials do, but soften over a fairly broad temperature range. This transition from a solid to a plastic-like behavior, called the transformation range, is distinguished by a continuous change in viscosity with temperature, thus in the scope of the present invention, the term melt as applied to the intermediate layer is used to encompass the temperature range where the material is fluid enough to readily flow under its own weight or pushed by the weight of an opposing liquid metal. This is a function of the glass chemistry, and preferably a glass chemistry that at the temperature of use will result in a glass viscosity between 10 and $10^3$ poise.

In the present invention, the function of the filler is to soften to a flowing viscosity upon exposure to the molten metal, temporarily forming a gob that recedes away and exposes the optical fiber. Both the liquidus and melting temperatures are general characterizations of the material property that allows for the forming gob to sufficiently recede from and thereby expose the optical fiber. Older gob material is floated away by the pressure of the denser molten metal, while new gob material is formed continually as the multilayer cored wire advances into the molten metal. The range of melting temperature of the filler is between 60 and 95% of the molten metal temperature, and preferably 80% of the melting temperature of the metal.

Example 1

The preferred method of creating the intermediate layer is to introduce 24 strands of E-glass consisting of a core of 16 parallel strands bundled about the optical fiber at its center and wrapped by 8 strands layered clockwise about the bundle. The weight of the combined fibers range between 30-40 g/meter. The number of filaments per yarn of fiber is denoted as its tow size. The tow size is generally given in terms of "K", or thousands of filaments. The metric unit of measure is TEX which is the weight in grams per kilometer (1,000 meters). The TEX of the preferred E-glass is 1420 (g/km).

The selection of tow and Tex are presented as an economic example. E-glass is a low alkali general purpose fiber with a melting temperature below approximately 1000° C. with an approximate composition as shown in FIG. 13. Although the molten nature of the intermediate layer can be achieved by a variety of materials known to those skilled in the art, a description of the general category of E-glass for the preferred embodiment of the present invention can be found in the publication of ASM Handbook, Vol. 21: Composites (#06781G), ASM International, 2001, and also in the publication of E_R_and_D_glass_properties.pdf (available from Saint-Gobain Vetrotex, Deutschland GmbH).

The outer cover is a metal with a Fe content greater than 50% with a wall thickness between 0.3 mm and 1.5 mm and an outer diameter between 10-14 mm. The outer cover is preferably low carbon steel of 1 mm wall thickness. The cover is wrapped about itself with a 3-4 mm overlapped lap seam, but can be closed with known closures such as lock seam.

Example 2

An alternate construction to introduce 24 strands of 1420 tex E-glass consisting of a core of 8 parallel strands bundled about the with 0.9 mm plastic semi-tight jacketed 62.5/125 μm graded index optical fiber at its center and wrapped by 8 strands layered clockwise about the bundle and an additional 8 strands wrapped counterclockwise about the latter wrap. The resulting weight is approximately 70 g/meters. The outer cover is a metal with a Fe content greater than 50% with a wall thickness between 0.3 mm and 1.5 mm and an outer diameter between 10-14 mm. The outer cover is preferably low carbon steel of 1 mm wall thickness. The cover is wrapped about itself with a 3-4 mm overlapped lap seam but can be closed with known closures such as lock seam.

Example 3

An alternate construction of 24 fiber strands with the 62.5/125 μm or alternately 50/125 μm graded index fiber with a 0.9 mm semi-tight tube arranged in the middle of a fiber bundle. Eight of the 16 fiber strands of the bundle are E-glass and 8 strands can be Ecomab, an alkali earth silicate, (AES), material available from Keramab, Haverheidelaan 4, B9140 Temse, BE, with a melting point of approximately 1330° C. A typical composition of AES material consists of 50-82% silica, 18-43% calcia and/or magnesia and less than 6% alumina, titania or zirconia and trace oxides. Wrapped about the bundle are an additional 8 more strands of E-glass. In total, 8 of 24 strands are AES, the balance of E-glass serving to lower the melting temperature of the mixed fibers. The density of the intermediate layer as constructed is approximately 0.51 g/cm$^3$. The intermediate fiber layer is then covered by a lap seam metal jacket tube of at least 50% Fe of approximately 1 mm.

It has been found that a molten gobular layer of material around the optical fiber flows away from the fiber at a predictable rate which is a function of its molten viscosity and the difference in density between it and the molten steel. In a practical sense, the difference in density of the molten metal and molten filler, although both are a function of temperature and composition, they are relatively constant within the application range of the interest. As the cored optical fiber is immersed into a molten steel bath, the outer jacket melts away exposing the filler which subsequently melts and pools around the optical fiber. Since the melting temperature of the filler is substantially lower than the molten metal temperature once exposed, this guarantees that it will always be in a molten state. It has become apparent that the small variation between the density of the steel and that of the molten gob results in a more predicable mechanism for exposing and renewing the fresh optical surface. The upward force of the displaced metal on the molten filler pushes the molten gob back and away from the optical core which stands extended from the gobular filler. As the feeding progresses, a sufficient quantity of molten filler accumulates at the base and a portion of this quantity is dragged with the extended optical core until the upward force of the molten metal upon the accumulated gob fractures the optical core at its unexposed base. The rate of exposed refreshed optical core is therefore more dependent upon the nearly constant density ratio gob/molten steel, allowing a wide tolerance for the rate of feed. It has been found that retraction of the molten gob from the advancing tip leads to more repeatable detection opportunities, rather than an anticipated destruction due to explosions, which relies on mechanical cutting of the tip to refresh the surface.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for measuring a temperature of a molten metal bath using a consumable cored wire, the consumable cored wire comprising an optical fiber, a metal pipe laterally surrounding the optical fiber, and an intermediate layer arranged between the metal pipe and the optical fiber, the intermediate layer comprising a plurality of fibers formed into a rope which fully encircles the optical fiber, the intermediate layer consisting of a material having a melting temperature in the range of between 60% and 95% of the molten metal temperature, the method comprising:

immersing the consumable cored wire into the molten metal bath, such that the metal pipe melts upon exposure to the molten metal bath and pieces of the intermediate layer are fluidized upon exposure to the molten metal bath, the fluidized pieces of the intermediate layer forming a molten gobular layer which flows away from the optical fiber and exposes an advancing tip of the optical fiber for measuring the temperature of the molten metal bath.

2. The method according to claim 1, wherein the material of the intermediate layer has a melting temperature in the range of between 1000° C. and 1500° C.

3. The method according to claim 2, wherein the material of the intermediate layer has a melting temperature in the range of between 1200° C. and 1400° C.

4. The method according to claim 1, wherein the molten gobular layer flows away from the optical fiber at a rate which is a function of a viscosity of the molten gobular layer and a difference between the density of the molten gobular layer and the density of the molten metal.

5. The method according to claim 4, wherein a ratio of the density of the molten gobular layer to the density of the molten metal is between 0.25 and 0.45.

6. The method according to claim 5, wherein the ratio of the density of the molten gobular layer to the density of the molten metal is 0.32 to 0.38.

7. The method according to claim 1, wherein a length of the rope is at least 500 meters.

8. The method according to claim 7, wherein the length of the rope is at least two kilometers.

9. The method according to claim 1, wherein the rope is composed of volumized strands.

10. The method according to claim 1, wherein the rope is formed from E-glass fibers.

11. The method according to claim 1, wherein the intermediate layer is arranged between the metal pipe and a tube formed from plastic or cardboard, and wherein the optical fiber is arranged within the plastic or cardboard tube.

12. The method according to claim 11, wherein an outer diameter of the optical fiber is smaller than an inner diameter of the plastic or cardboard tube, such that the optical fiber is moveable within the plastic or cardboard tube.

13. The method according to claim 1, where the metal pipe comprises a metal having a Fe content greater than 50%, and wherein the metal pipe has a wall thickness between 0.3 mm and 1.5 mm and an outer diameter between 10 to 14 mm.

* * * * *